United States Patent
Xiang et al.

(10) Patent No.: US 11,052,120 B2
(45) Date of Patent: Jul. 6, 2021

(54) METHOD OF COMMITTED DIFFERENTIATION OF HUMAN INDUCED PLURIPOTENT STEM CELLS INTO LEYDIG CELLS AND APPLICATION OF LEYDIG CELLS

(71) Applicant: SUN YAT-SEN UNIVERSITY, Guangdong (CN)

(72) Inventors: Peng Xiang, Guangdong (CN); Mei Hua Jiang, Guangdong (CN); Weiqiang Li, Guangdong (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 342 days.

(21) Appl. No.: 15/987,953

(22) Filed: May 24, 2018

(65) Prior Publication Data

US 2018/0311286 A1    Nov. 1, 2018

Related U.S. Application Data

(63) Continuation of application No. PCT/CN2016/107361, filed on Nov. 25, 2016.

(30) Foreign Application Priority Data

Nov. 27, 2015    (CN) .......................... 201510845021.8

(51) Int. Cl.
| | |
|---|---|
| C12N 5/00 | (2006.01) |
| C12N 5/02 | (2006.01) |
| A61K 35/52 | (2015.01) |
| C12N 5/071 | (2010.01) |
| A61K 45/00 | (2006.01) |
| A61P 5/26 | (2006.01) |
| C12N 5/0735 | (2010.01) |
| A61K 38/18 | (2006.01) |

(52) U.S. Cl.
CPC .............. *A61K 35/52* (2013.01); *A61K 45/00* (2013.01); *A61P 5/26* (2018.01); *C12N 5/0606* (2013.01); *C12N 5/0683* (2013.01); *A61K 38/1808* (2013.01); *A61K 38/1825* (2013.01); *C12N 2500/32* (2013.01); *C12N 2500/44* (2013.01); *C12N 2500/99* (2013.01); *C12N 2501/105* (2013.01); *C12N 2501/11* (2013.01); *C12N 2501/115* (2013.01); *C12N 2501/135* (2013.01); *C12N 2501/31* (2013.01); *C12N 2501/395* (2013.01); *C12N 2501/727* (2013.01); *C12N 2506/45* (2013.01); *C12N 2513/00* (2013.01); *C12N 2533/32* (2013.01); *C12N 2533/52* (2013.01); *C12N 2533/54* (2013.01)

(58) Field of Classification Search
CPC ..... A61K 35/52; C12N 5/0683; C12N 5/0606
See application file for complete search history.

(56) References Cited

FOREIGN PATENT DOCUMENTS

| | | |
|---|---|---|
| CN | 101892190 A | 11/2010 |
| CN | 102174468 A | 9/2011 |

OTHER PUBLICATIONS

Sonoyama, 2012, Endocrinology, 153:4336-45.*
Koehler (2011, BMC Neuroscience, 12:82, pp. 1-14).*
Liu (2012, Stem Cells Translational Medicine, 1:266-278).*
Ren-Shan GE et al., In search of rat stem Leydig cells: identification, isolation, and lineage-specific development, Proc Natl Acad Sci, Feb. 21, 2006, pp. 2719-2724, vol. 103, No. 8.
Erin Stanley et al., Identification, proliferation, and differentiation of adult Leydig stem cells, Endocrinology, Oct. 2012, pp. 5002-5010, vol. 153, No. 10.
Ivraym B. Barsoum et al., Fetal Leydig cells: progenitor cell maintenance and differentiation, Journal of Andrology, Jan./Feb. 2010, pp. 11-15, vol. 31, No. 1.
Michail S. Davidoff, et al., Progenitor cells of the testosterone-producing Leydig cells revealed, The Journal of Cell Biology, Dec. 6, 2004, pp. 935-944, vol. 167, No. 5.
Wang, Yu-Yun et al., Induced differentiation of human adipose-derived stem cells into Leydig cells in vitro, National Journal of Andrology, Sep. 1, 2012, pp. 811-815, vol. 18, No. 9, Abstract Only; document not in English.
Takashi Yazawa et al., Differentiation of Adult Stem Cells Derived from Bone Marrow Stroma into Leydig or Adrenocortical Cells, Endocrinology, Jan. 1, 2006, pp. 4104-4111, vol. 147, No. 9.
Search Report of European Patent Application No. 16868053.6 dated Oct. 30, 2018.
Yan Yang et al., Directed Mouse Embryonic Stem Cells into Leydig-Like Cells Rescue Testosterone-Deficient Male Rats In Vivo, Stem Cells and Development, Oct. 23, 2014, pp. 459-470, vol. 24, No. 4.

* cited by examiner

*Primary Examiner* — Valarie E Bertoglio
(74) *Attorney, Agent, or Firm* — Metis IP LLC

(57) ABSTRACT

The present application provides an in-vitro committed differentiation method for inducing human induced pluripotent stem cells (hiPSCs) into Leydig cells (LCs) by neural crest stem cells (NCSCs). The hiPS-derived LCs is verified by an animal model to have the capacity of regenerating senile or injured LCs, so that a new treatment for supplementing testosterone is provided for patients suffering from hypogonadism, particularly for patients suffering from late-onset hypogonadism (LOH).

14 Claims, 5 Drawing Sheets

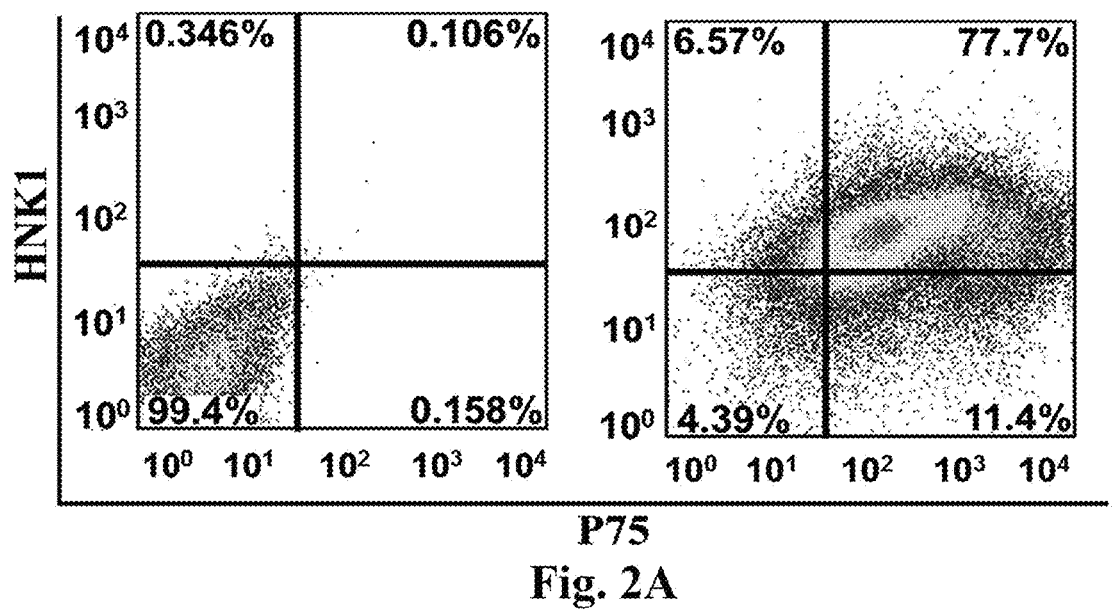
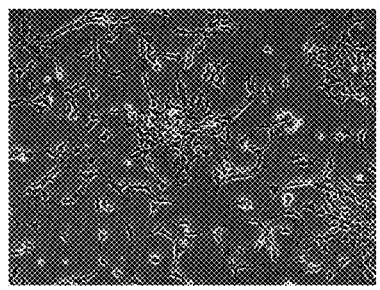 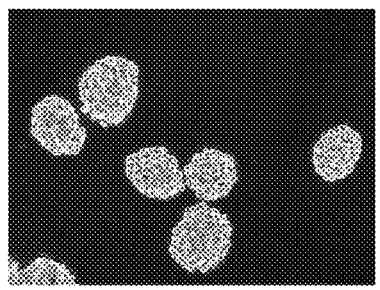
Fig. 2B    Fig. 2C
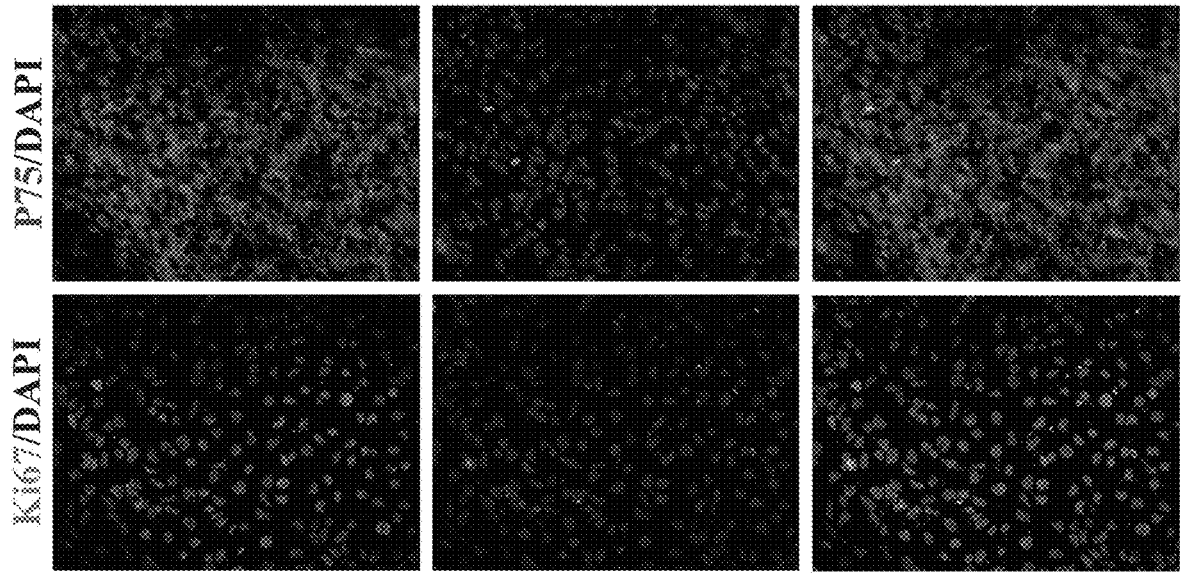
Fig. 2D

METHOD OF COMMITTED DIFFERENTIATION OF HUMAN INDUCED PLURIPOTENT STEM CELLS INTO LEYDIG CELLS AND APPLICATION OF LEYDIG CELLS

CROSS REFERENCES TO RELATED APPLICATIONS

This application is a continuation application of PCT Application No. PCT/CN2016/107361 filed on Nov. 25, 2016, which claims the benefit of Chinese Patent Application No. 201510845021.8 filed on Nov. 27, 2015. The entire contents of the above applications are hereby incorporated by reference in their entirety.

FIELD OF THE INVENTION

The present application relates to the technical field of stem cells and tissue engineering, and more particularly relates to a method of committed differentiation of human induced pluripotent stem cells into Leydig cells (LCs) and application of the LCs.

BACKGROUND OF THE INVENTION

Leydig cells (LCs) are distributed on loose connective tissues between testicular spermatogenic tubules, and testosterone secreted by the LCs is a main source of testosterone in adult males. At present, a main therapy for late-onset hypogonadism (LOH) adopts an exogenous androgen replacement therapy by injecting medicines, but it has the defects that the supplemental dose is hard to control, and it is still difficult to mimic physiological testosterone secretion and characteristics. LOH patients have to take androgen drugs for a long time, which may cause various complications and side effects. Therefore, only a small number of patients with androgen deficiency receiving exogenous testosterone therapy, so researchers have sought to develop alternative treatment methods for the long—lasting delivery of androgens. LCs transplantation is the best way to treat testosterone deficiency-related diseases such as the LOH, and it can better simulate the physiological characteristics of human testosterone secretion, effectively increase the serum and intratesticular testosterone concentration, achieve a better therapeutic effect and avoid negative effects produced in a therapeutic process as much as possible. However, the unresolved issues including unclear development origin, difficulty in obtaining human tissues for primary culture, small number, and difficulty in expansion greatly restrain the clinical translation of the LCs. A conventional separation method of the LCs adopts a density gradient centrifugation method (Ge R S, Dong Q, Sottas C M, Papadopoulos V, Zirkin B R, Hardy M P. In search of rat stem Leydig cells: identification, isolation, and lineage-specific development. Proc Natl Acad Sci USA 2006; 103: 2719-2724; Stanley E, Lin C Y, Jin S, Liu J, Sottas C M, Ge R, et al. Identification, proliferation, and differentiation of adult Leydig stem cells. Endocrinology 2012; 153: 5002-5010.).

Induced pluripotent stem (iPS) cells have self-renewal and multi-directional differentiation potentials similar to that of embryonic stem cells; in addition. As generated from autologous adult cells, the iPS cells avoid many of the restrictions including immunogenic rejection and ethical concerns that have hampered the clinical applications of embryonic stem cells, and become important cell sources for discovering pathogenesis and developing new cell replacement treatment of human diseases. Patient-derived cells are transduced with transcription factors (KLF4, SOX2, OCT4 and c-MYC) and then are reprogrammed into pluripotent stem cells, thereby making auto-transplantation possible. The iPS cells are used as "seed" cells, which can be greatly amplified in vitro and are subjected to differentiated into specific tissue cells.

Possible sources of the LCs include adrenal-gonadal primordium, neural crests, mesonephros or coelomic epithelium [Barsoum, I. B. and H. H. Yao, Fetal Leydig cells: progenitor cell maintenance and differentiation. J Androl, 2010. 31(1): p. 11-5.]. The research of Davidoff have found that progenitor leydig cells express neural stem cell markers Nestin and pericyte markers NG2, which further verifies that the LCs may be derived from neural crest [Davidoff, M. S., Middendorff, R., Enikolopov, G., Riethmacher, D., Holstein, A. F., Muller, D., Progenitor cells of the testosterone-producing Leydig cells revealed. J Cell Biol, 2004. 167(5): p. 935-44.].

SUMMARY OF THE INVENTION

The inventor finds that iPS cells can be induced to differentiate into mature LCs through a intermediate stage of neural crest stem cells (NCSCs) in vitro. The present application is directed to provide an in-vitro committed differentiation method for differentiating human hiPS cells into NCSCs, the latter of which are then induced to differentiate to the LCs, and the function of hiPS-derived LCs is verified by an animal model to test whether hiPS-derived LCs have the capacity of regenerating senile or injured LCs, so that a new therapy for testosterone supplement can be provided for patients suffering from hypogonadism, particularly for patients suffering from LOH.

The present application is implemented by the following technical solution:

A method of committed differentiation of hiPS cells into LCs (hiPS-hNCSCs-LCs) is provided according to one aspect of the present application.

In a further implementation solution, the above-mentioned method is mainly that the hiPS cells are used as "seed" cells; firstly, the hiPS cells are induced to differentiate into obtain specific tissue cells; the specific tissue cells may be further directionally differentiated into LCs in vitro; and more concrete, the specific tissue cells are human NCSCs.

In a further implementation solution, a method for inducing human-induced pluripotent stem cells (hiPSCs) differentiate to Leydig cells (hiPS-hNCSCs-LCs) specifically includes:

(1) performing committed differentiation of the human-induced pluripotent stem cells (hiPSCs) to obtain human neural crest stem cells (hiPS-hNCSCs);

(2) performing committed differentiation of the human neural crest stem cells (hiPS-hNCSCs) obtained in the step (1) to obtain the Leydig cells (hiPS-hNCSCs-LCs).

In a further implementation solution, the step (1) includes: inoculating the human induced pluripotent stem cells (hiPSCs) into a culture dish with low attachment surface for culture, and a Petri culture dish is preferred.

In a further implementation solution, the step (1) includes: performing committed differentiation of the human induced pluripotent stem cells (hiPSCs) in a neural differentiation culture medium to obtain the human neural crest stem cells (hiPS-hNCSCs).

In a further implementation solution, the step (1) includes: culturing the human induced pluripotent stem cells (hiPSCs)

in the neural differentiation culture medium to form embryoid bodies (EBs), and then performing adherent culture of EBs with a neutral crest stem cell culture medium.

In one specific implementation solution, the step (1) of the committed differentiation method of the human induced pluripotent stem cells (hiPSCs) to the Leydig cells (hiPS-hNCSCs-LCs) includes: digesting and then resuspending the human induced pluripotent stem cells (hiPSCs), inoculating suspension cells into the culture dish with low attachment surface, preferably inoculating the cells into the Petri culture dish, performing suspension culture by the neural differentiation culture medium to form the embryoid bodies, then inoculating the embryoid bodies into a fibronectin-coated culture plate, performing adherent culture by using the neural crest stem cell culture medium, and sorting P75/HNK1 double-positive cells through a flow cytometry from differentiated cell population subjected to the adherent culture, and the P75+/HNK1+cells are the human neural crest stem cells (hiPS-hNCSCs).

In one specific implementation solution, the human induced pluripotent stem cells (hiPSCs) are resuspended by a ROCK inhibitor-containing mTeSR culture medium.

The neural differentiation culture medium may adopt the one which is known in this field. In one preferred implementation solution, the neural differentiation culture medium contains 50 to 80 percent (V/V) of Knockout DMEM, 5 to 20 percent (V/V) of Knockout SR, 0.5 to 5 percent (V/V) of Penicillin-Streptomycin solution, 0.5 to 5 mM of L-glutamine, and 0.05 to 0.5 mM of β-mercaptoethanol. In a further preferred implementation solution, neural differentiation culture medium contains 80 percent (V/V) of Knockout™ DMEM, 18 percent (V/V) of Knockout™ SR, 1 percent (V/V) of Penicillin-Streptomycin solution, 1 mM of L-glutamine, and 0.1 mM of β-mercaptoethanol.

The neural crest stem cell culture medium may adopt the one which is known in this field. In one preferred implementation solution, the neural crest stem cell culture medium is obtained by mixing a DMEM-F12 culture medium with a Neurobasal culture medium in a ratio of 1:0.1-1. In a further preferred implementation solution, the neural crest stem cell culture medium is obtained by mixing the DMEM-F12 culture medium with the Neurobasal culture medium in a ratio of 1:1.

In a further preferred implementation solution, the neural crest stem cell culture medium contains 0.1 to 5 percent (V/V) of N2, 0.5 to 10 percent (V/V) of B27, 0.5 to 5 percent (V/V) of Penicillin-Streptomycin solution, 0.5 to 5 mM of L-glutamine, and 0.05 to 0.5 mM of β-mercaptoethanol, and is further added with 1 to 100 ng/mL of basic fibroblast growth factor (bFGF) and 1 to 100 ng/mL of epidermal growth factor (EGF). Preferably, the neural crest stem cell culture medium contains 1 percent (V/V) of N2, 2 percent (V/V) of B27, 1 percent (V/V) of mycillin mixed medium, 1 mM of L-glutamine, and 0.1 mM of β-mercaptoethanol, and is further added with 10 ng/mL of the bFGF and 10 ng/mL of the EGF.

In a further preferred implementation solution, the neural crest stem cell culture medium is obtained by mixing the DMEM-F12 culture medium with the Neurobasal culture medium in a ratio of 1:0.1-1, adding 0.1 to 5 percent (V/V) of N2, 0.5 to 10 percent (V/V) of B27, 0.5 to 5 percent (V/V) of Penicillin-Streptomycin solution, 0.5 to 5 mM of L-glutamine, and 0.05 to 0.5 mM of β-mercaptoethanol, and further adding 1 to 100 ng/mL of the bFGF and 1 to 100 ng/mL of the EGF.

In one specific implementation solution, the neural crest stem cell culture medium is obtained by mixing the DMEM-F12 culture medium with the Neurobasal culture medium in the ratio of 1:1, adding 1 percent (V/V) of N2, 2 percent (V/V) of B27, 1 percent (V/V) of Penicillin-Streptomycin solution, 1 mM of L-glutamine, and 0.1 mM of β-mercaptoethanol, and further adding 10 ng/mL of the bFGF and 10 ng/mL of the EGF.

In one specific implementation solution, after being formed for 5 days, the embryoid bodies are inoculated into the fibronectin-coated culture plate. In one preferred implementation solution, the fibronectin-coated culture plate is coated by polylysine/gelatin/fibronectin.

In one specific implementation solution, after being adhered for 5 to 7 days, the cells subjected to the adherent culture are sorted by using the flow cytometry.

In one specific implementation solution, the step (2) of the committed differentiation method of the human-induced pluripotent stem cells (hiPSCs) to the Leydig cells (hiPS-hNCSCs-LCs) includes: amplifying the human neural crest stem cells (hiPS-hNCSCs) obtained in the step (1), and then replacing the culture medium by a Leydig cells (LCs) differentiation culture medium to obtain the Leydig cells (hiPS-hNCSCs-LCs).

In one specific implementation solution, in the step (2), when the human neural crest stem cells (hiPS-hNCSCs) are amplified to reach a density of 60% confluence, the culture medium is replaced by the LC differentiation culture medium.

In a preferred implementation solution, the LCs differentiation culture medium is obtained by adding 0.1 to 20 percent (V/V) of fetal calf serum (FCS), 0.1 to 10 nM of triiodothyronine (T3), 0.1 to 20 ng/ml of luteinizing hormone (LH), 5 to 100 ng/ml of an insulin-like growth factor (IGF-I), and 1 to 50 ng/ml of a platelet-derived growth factor BB (PDGFBB) into the DMEM-F12 culture medium.

In a preferred implementation solution, the LCs differentiation culture medium is obtained by adding 2 percent (V/V) of FCS, 1 nM of T3, 1 ng/ml of LH, 70 ng/ml of the IGF-I, and 10 ng/ml of the PDGF-BB into the DMEM-F12 culture medium.

In one specific implementation solution, the induction time in the step (2) is 14 days.

A method of treating relevant diseases caused by low testosterone level which comprises administrating an effective amount of the Leydig cells (hiPS-hNCSCs-LCs) obtained by the method according to claim 1; and a drug for treating relevant diseases caused by low testosterone level which comprises an effective amount of the Leydig cells (hiPS-hNCSCs-LCs) obtained by the method according to claim 1 are further provided according to another aspect of the present application.

In one specific implementation solution, Leydig cells (hiPS-hNCSCs-LCs) of the present application may increase the level of serum testosterone.

The "hNCSCs" or "hiPS-hNCSCs" used in the present application means human neural crest stem cells (hNCSCs) obtained by the committed differentiation of human-induced pluripotent stem cells (hiPSCs).

The "hiPS-hNCSCs-LCs" or "hNCSCs-LCs" used in the present application means Leydig cells (LCs) obtained by the induced differentiation of the human neural crest stem cells (hNCSCs) obtained by performing the differentiation on the human-induced pluripotent stem cells (hiPSCs).

In this solution of the present application, a human iPS cell line is induced to differentiate into the neural crest stem cells (hNCSCs) which are further subjected to differentiate into the Leydig cells (LCs), with specific steps of:

(1) performing committed differentiation on the human iPS cell line (hiPSCs) to obtain the neural crest stem cells (hNCSCs or hiPS-hNCSCs):

a. preparation of cell suspension: digesting the iPS cell line (hiPSCs) into small masses, and resuspending them;

wherein cells may be resuspended by a ROCK inhibitor-containing mTeSR culture medium.

b. Committed differentiation: inoculating the suspension cells into a culture dish with low attachment surface, and culturing the cells by using a neural differentiation culture medium to form embryoid bodies;

wherein the neural differentiation culture medium may for example contain 80 percent of Knockout™ DMEM, 18 percent of Knockout™ SR, 1 percent (V/V) of a dual antibody, 1 mM of L-glutamine, and 0.1 mM of β-mercaptoethanol.

c. Adherent culture: inoculating the formed embryoid bodies into a fibronectin-coated culture plate for adherent culture;

Embryoid bodies were cultured for 5 days in ultra-lowattachment culture dishes with daily changes of medium. The culture plate may be coated with polylysine/gelatin/fibronectin. The neural crest stem cell culture medium may be added into the culture plate. The neural crest stem cell culture medium may be obtained by mixing a DMEM/F12 culture medium with a Neurobasal culture medium in a ratio of 1:1, is added with 1 percent (V/V) of N2, 2 percent (V/V) of B27, 1 percent (V/V) of a Penicillin-Streptomycin solution, 1 mM of L-glutamine, and 0.1 mM of β-mercaptoethanol, and is further added with 10 ng/mL of a basic fibroblast growth factor (bFGF) and 10 ng/mL of an epidermal growth factor (EGF).

d. Flow sorting: sorting cells of P75+/HNK1+by using flow cytometry, wherein the cells are the neural crest stem cells (hNCSCs or hiPS-hNCSCs).

The neural crest stem cell culture medium may be obtained by mixing the DMEM/F12 culture medium with the Neurobasal culture medium in the ratio of 1:1, is added with 1 percent (V/V) of N2, 2 percent (V/V) of B27, 1 percent (V/V) of the Penicillin-Streptomycin solution, 1 mM of L-glutamine, and 0.1 mM of β-mercaptoethanol, and is further added with 10 ng/mL of the bFGF and 10 ng/mL of the EGF.

(2) performing committed differentiation on the neural crest stem cells (hNCSCs or hiPS-hNCSCs) obtained in the step (1) to the Leydig cells (hiPS-hNCSCs-LC s or hNCSCs-LCs).

The step (2) may include: Expansion the neural crest stem cells (hNCSCs) obtained in the step (1), and performing differentiation in a Leydig cells (LCs) differentiation culture medium for 14 days, thus obtaining the Leydig cells (NCSCs-LCs), wherein the obtained neural crest stem cells (hNCSCs) may be expansioned in the neural crest stem cell culture medium. Further, when the hNCSCs are expansioned to reach a density of 60% confluence, the neural crest stem cell culture medium is replaced by the LCs differentiation culture medium. The LCs differentiation culture medium may be obtained by adding 0.1 to 20 (V/V) percent of fetal calf serum (FCS), 0.1 to 10 nM of triiodothyronine (T3), 0.1 to 20 ng/ml of luteinizing hormone (LH), 5 to 100 ng/ml of an insulin-like growth factor (IGF-I), and 1 to 50 ng/ml of a platelet-derived growth factor BB (PDGFBB) into the DMEM-F12 culture medium. The obtained hNCSCs-LCs express 3β-HSD, P450C17, StAR and SF-1, and secrete testosterone.

The Leydig cells (hiPS-hNCSCs-LCs) obtained by the method of the present application are transplanted to a Leydig cell-removed rat animal model (which is a Leydig cell apoptosis model established by applying a specific apoptosis inducer ethane dimethyl sulfonate (EDS) for the Leydig cells of a rat, namely an EDS model) to evaluate the effect of the cells in a testicular microenvironment. A result shows that after the cells are transplanted, the concentration of serum testosterone can be increased, so that the Leydig cells (hiPS-hNCSCs-LCs) obtained by the method of the present application may be used as the medicines for treating the relevant diseases caused by low testosterone level.

In the present application, the human iPS cells are subjected to neural crest differentiation and the cell sorting to obtain the neural crest stem cells, and the neural crest stem cells are then subjected to the leydig cell differentiation in the in-vitro culture medium to obtain the Leydig cells with the function of secreting testosterone. The Leydig cells (hiPS-hNCSCs-LCs) of the present application are transplanted into the rat model in which the Leydig cells are eliminated by the EDS, so that the serum testosterone level of the model animal may be increased.

The "V/V" described in this text is volume percent of each component in the culture solution or the culture medium.

Through long-term and intensive study by researchers of the present application, a new idea is provided for the treatment of testosterone deficiency diseases such as the LOH, namely the human induced pluripotent stem cells (hiPSCs) are used as cell sources of the Leydig cells (LCs), and an experiment shows that the hiPS-derived LCs have the capacity of regenerating senile or injured LCs, and can better simulate the physiological characteristic of human testosterone secretion, so that the serum and intratesticular testosterone concentration are effectively restored. A better therapeutic effect is achieved, and negative effects produced in a therapeutic process can be avoided as much as possible. Therefore, on one hand, the defects of using a conventional exogenous androgen drug including the difficulty in simulating the physiological conditions of testosterone of organisms, uncontrolled supplemental dose, long-term intakes, and various complications and side effects are overcome, and on the other hand, the defects of unclear LC developmental origin, difficulty in obtaining human tissues for primary cultire, small number, and difficulty in expansion are also overcome.

BRIEF DESCRIPTION OF THE DRAWINGS

FIG. 1A. hiPSCs subjected to expansion culture, FIG. 1B. the embryoid body subjected to suspension culture, FIG. 1C. the embryoid body subjected to adherent culture, which forms a neural rossette structure and cells is migrated out, FIG. 1D. expressions (immunofluorescent staining) of NCSCs specific markers in the differentiated cells, wherein Scale bar is equal to 100 μm.

FIG. 2A-FIG. 2D show phase contrast and fluorescent staining photos of biological characteristic analysis of hNCSCs. FIG. 2A. expressions of HNK1 and P75 of NCSCs detected by a flow cytometry in hiPSCs; FIG. 2B. a phase contrast photo of hNCSCs subjected to adherent culture after flow cytometry; FIG. 2C. a phase contrast photo of hNCSCs after suspension culture; FIG. 2D. expression of specific markers P75 and Sox10 of NCSCs in hNCSCs subjected to expansion culture, wherein Scale bar is equal to 100 μm.

FIG. 3A. cell shapes, observed under a phase contrast microscope, of hNCSCs before and after differentiation to the peripheral neurons, and FIG. 3B to FIG. 3D are immunofluorescent staining results: FIG. 3B. hNCSCs differentiated into peripherin+/Tuj1+peripheral neurons, FIG. 3C. hNCSCs differentiated into TH+/Tuj1+ peripheral sympathetic neurons, and FIG. 3D. hNCSCs differentiated into GFAP+/S100B+schwann cells, wherein Scale bar is equal to 100 μm.

FIG. 4A. cell shapes, observed under a phase contrast microscope, of hNCSCs before and after differentiation to hNCSCs-MSC; FIG. 4B. an Alizarin Red S staining graph, a Tuluidine Blue staining graph and an Oil Red O staining graph which are obtained by culturing hNCSCs-MSC in a proper differentiation medium for a period of time by using a chemical staining method; FIG. 4C. an αSMA staining graph obtained by culturing hNCSCs-MSC in a proper differentiation medium for a period of time, wherein Scale bar is equal to 100 μμm.

DETAILED DESCRIPTION OF ILLUSTRATED EMBODIMENTS☐

It can be understood that specific implementation modes described herein are only expressed by means of examples, but not deemed as limitations to the prevent application. Main features of the present application can be used for various implementation modes without departing from the scope of the present application. Persons skilled in the art will realize or can confirm that many equivalents may be all applied into the specific steps described in this text only by using conventional experiments. These equivalents are deemed as falling within the scope of the present application, and are covered by claims.

For the purpose of making objectives, technical solutions and advantages of the present application clearer and more understandable, a further detailed description will be made below to the present application in combination with specific implementation modes and with reference to accompanying drawings. It should be understood that these descriptions are only examples, but not intended to limit the scope of the present application. In addition, in the descriptions below, descriptions of known structures and technologies are omitted to avoid unnecessary confusion of the concept of the present application.

Embodiment 1

Differentiation From a Human-induced Pluripotent Stem (hiPS) Cell Line to Human Neural Crest Stem Cells (hNCSCs)

Figure 1A:
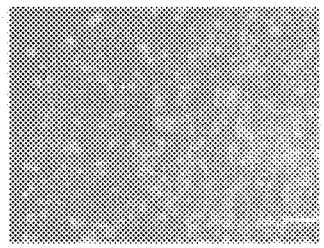
FIG. 1A-FIG. 1D show phase contrast photos of formation of an embryoid body in suspension culture in an the differentiation process of human-induced Pluripotent stem cells (hiPSCs) to human neural crest stem cells (hNCSCs) and immunofluorescent staining graphs of differentiated NCSCs markers, wherein pictures from FIG. 1A to FIG. 1C are the phase contrast photos.

(1) preparation of cell suspension: with an established human iPS cell line (hiPSCs, Hum Mol Genet. 2013,22(11): 2221 -33), human induced pluripotent stem cells (hiPSCs) grew in a flat cloning form when subjected to expansion culture on Matrigel, and were closely arrayed, as shown in FIG. 1A. The hiPSCs were digested into small masses with EDTA at the concentration of 0.5 mmol/L, and were resuspended by a ROCK inhibitor-containing mTeSR culture medium, wherein a used ROCK inhibitor is Y27632 (Calbiochem, San Diego, Calif.).

Figure 1B:
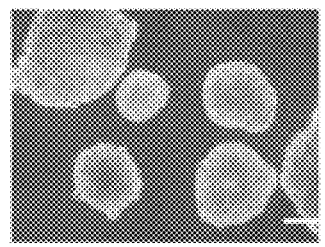

(2) committed differentiation: suspension cells were collected, then inoculated in a Petri culture dish, and subjected to suspension culture by a neural differentiation culture medium (80 percent of Knockout™ DMEM, 18 percent of Knockout™ SR, 1 percent (V/V) of Penicillin-Streptomycin solution, 1 mM of L-glutamine, and 0.1 mM of β-mercaptoethanol), thus forming brightly spherical embryoid bodies, as shown in FIG. 1B (the neural differentiation culture medium in this embodiment is not limited to the above-mentioned formula, and may still achieve the effect as shown in FIG. 1B when adopting any one of specific combinations of the neural differentiation culture medium containing 50 to 80 volume percent of Knockout DMEM, 5 to 20 volume percent of Knockout SR, 0.5 to 5 volume percent of Penicillin-Streptomycin solution, 0.5 to 5 mM of L-glutamine, and 0.05 to 0.5 mM of β-mercaptoethanol of the present application), wherein Knockout™ DMEM and Knockout™ SR are both purchased from Invitrogen, Carlsbad, Calif.

Figure 1C:
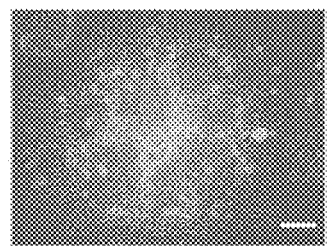

(3) adherent culture: 5 days after the embryoid body was formed by the suspension culture, the spherical embryoid body was inoculated into a culture plate coated with polylysine/gelatin/fibronectin for adherent culture; a neural crest stem cell culture medium (obtained by mixing a DMEM-F12 culture medium and a Neurobasal culture medium according to a ratio of 1:1, adding 1 percent (V/V) of N2, 2 percent (V/V) of B27, 1 percent (V/V) of Penicillin-Streptomycin solution, 1 mM of L-glutamine, and 0.1 mM of β-mercaptoethanol, and further adding 10 ng/mL of a basic fibroblast growth factor (bFGF) (Invitrogen, 13256029) and 10 ng/mL of an epidermal growth factor (EGF) (PeproTech, NO. 62253-63-8)) were used, and then changed every other day. After the adherent culture was carried out for 2 days, it could be seen that obvious neural rossette structures appeared at the central parts of cell masses, and the cells were migrated out, as shown in FIG. 1C. (The neural crest stem cell culture medium in this embodiment is not limited to the above-mentioned formula, and may still achieve the effect as shown in FIG. 1C when adopting any one of specific combinations of the neural crest stem cell culture medium which is obtained by mixing the DMEM-F12 culture medium with the Neurobasal culture medium in a ratio of 1:0.1-1, adding 0.1 to 5 volume percent of N2, 0.5 to 10 volume percent of B27, 0.5 to 5 volume percent of Penicillin-Streptomycin solution, 0.5 to 5 mM of L-glutamine, and 0.05 to 0.5 mM of β-mercaptoethanol, and further adding 1 to 100 ng/mL of the bFGF and 1 to 100 ng/mL of the EGF.)

Figure 1D:
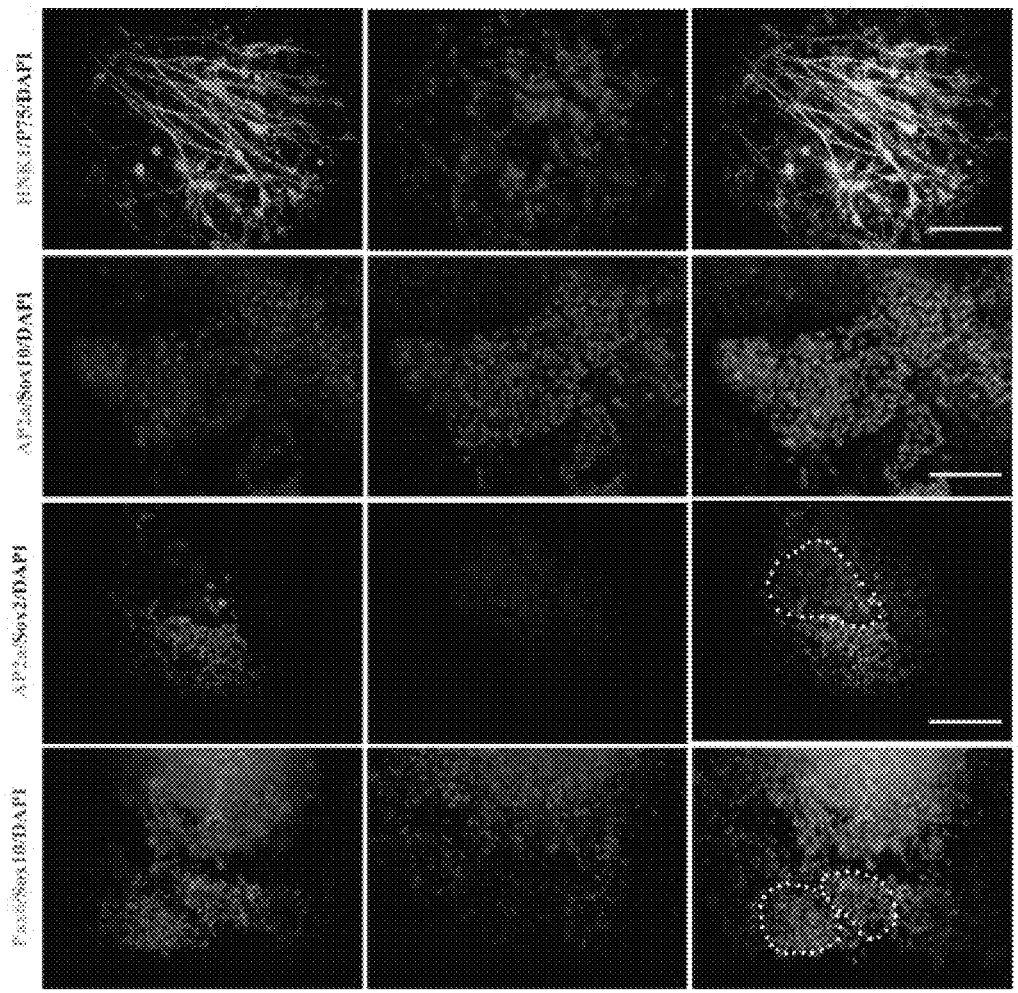

Immunofluorescent staining detection carried out on the cells subjected to the adherent culture found that as shown in FIG. 1D, markers such as Pax6 and Sox2 were mainly expressed in cells at the central parts of neural rosette structures , and specific markers such as AP2α, Sox10, P75 and HNK1 of neural crest stem cells were mainly expressed in outwards migrated cells, thus indicating that after the embryoid body culture stage and then the adherent culture, the hiPSCs might become hNCSCs through differentiation.

(4) flow cytometry cell sorting: after the adherent culture was carried out for 5 days, the embryoid body was digested into single cells, the cells were labeled with anti-P75 and -HNK1 antibodies, and then P75+/HNK1+double positive cells was isolated by flow cytometry cell sorting. During cell sorting, the culture medium was removed by a sucker; the cells were washed with PBS twice, and then Accutase was added to digest the differentiated hiPSCs for 3 to 5 minutes in 37° C. it was observed that the cells turned into round and bright; a culture medium was added to stop the digestion, and the cells were resuspended; then the cells were filtered by a nylon sieve, and were centrifugated at 1,500 rmp for 5 min; supernatant was abandoned, and 1 mL of PBS was added and the cells were resuspended uniformly; and 20 µL of cell suspension was used for cell counting. The residual cells were divided into four groups for antibody labeling: an IgG negative control group, a P75 antibody single-label group, an HNK1 antibody single-label group and a P75+/HNK1+ antibody sample group, and 20 µL of antibody was added to label every 106 cells. A flow cytometry (BD influx cell sorter) was firstly used for performing flow sample injection on the cell suspension in the IgG negative control group to sort out a negative fluorescence signal region serving as a negative control, and cells having the fluorescence intensity which was 10 or higher times that of the negative control were collected. Flow detection analysis showed that after the differentiation, about 80 to 90 percent of hiPSCs expressed the specific markers HNK1 and P75 (FIG. 2A) of NCSC, thus indicating that most cells have been differentiated into hNCSCs after the differentiation.

Purified hNCSCs might be obtained through cell sorting, and the adherent culture was performed according to $5 \times 10^4$ to $1 \times 10^5$ cell/cm$^2$. As shown in FIG. 2B, the cells in the adherent culture were relatively uniform in shape. After being subjected to digestion and passage, the hNCSCs were inoculated into a low-attachment culture plate. As shown in FIG. 2C, the cells formed neural spheres with relatively uniform sizes. The hNCSCs obtained by cell sorting were subjected to immunofluorescence detection. As shown in FIG. 2D, it can be seen that the cells maintained the expression of the specific markers of NCSCs including P75, Sox10. It indicates that under the existing culture and expansion conditions, the cells may sustain the characteristics of the NCSCs.

Figure 3A:
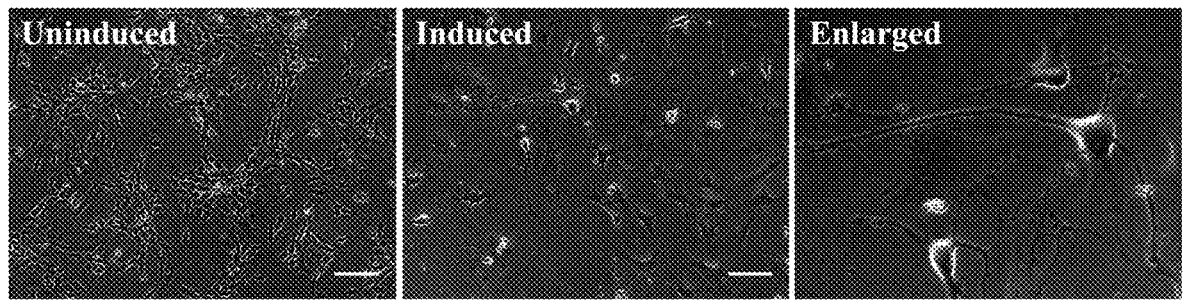
FIG. 3A-FIG. 3D show a graph of and immunofluorescent staining photos of hNCSCs differentiated to peripheral neurons and schwann cells.
Figure 3B:
Figure 3C:
Figure 3D:
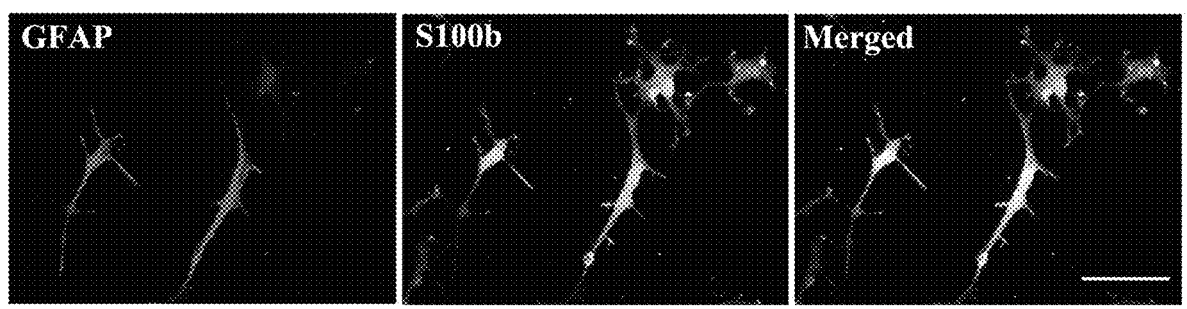

Biological characterization was performed on the hNCSCs. After the hNCSCs were inoculated into a culture plate coated with polylysine/gelatin/fibronectin, the culture medium was replaced by a induction medium for further differentiation. As shown in FIG. 3A, after the NCSCs were subjected to the peripheral neurons differentiation for 2 weeks, it could be seen that the cells had obvious changes in their morphology: cell bodies were rounded, and had neuronal fibers. After 3 to 4 weeks, the cells were used for immunostaining. As shown in FIGS. 3B and 3C, it can be seen that there were peripherin+/Tuj1+peripheral neurons and TH+/Tuj1+sympathetic neurons. The hNCSCs were subjected to differentiation in schwann cell induction medium, and then were detected by immunostaining after 4 weeks. As shown in FIG. 3D, it can be seen that there were GFAP+/S100b+schwann cells.

Figure 4A:
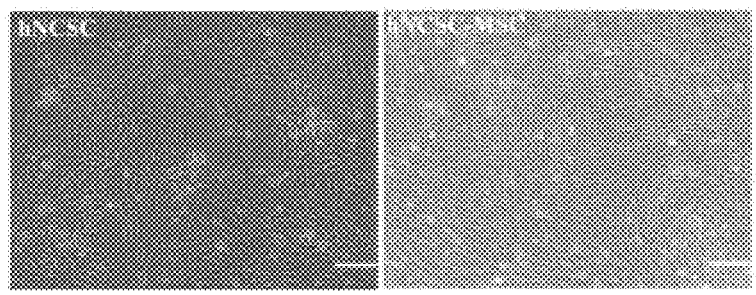
FIG. 4A-FIG. 4C show phase contrast and histochemical staining photos of hNCSCs differentiated into hNCSCs-MSC.
Figure 4B:
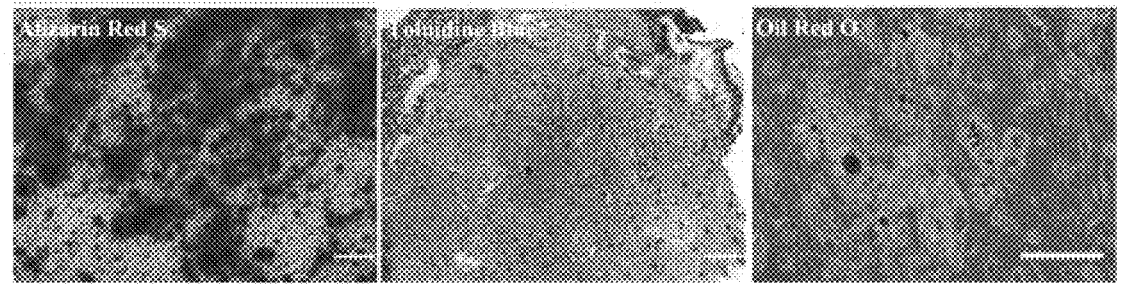
Figure 4C:
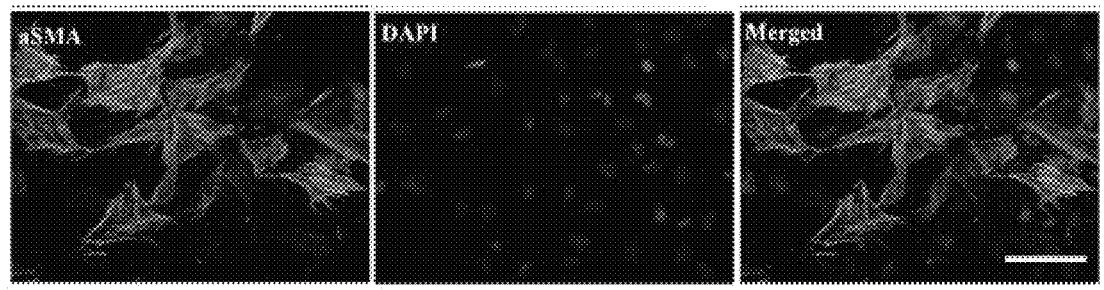

After being subjected to differentiation in a mesenchymal stem cell (MSC) culture medium (low-glucose DMEM, 10 percent of FBS) for 7 days, the hNCSCs were differentiated into MSCs. As shown in FIG. 4A, it can be seen that the cells turned into spindle-shaped and were in swirling growth. The multidirectional differentiation capacity of the MSCs (hNCSCs-MSC) induced from the hNCSCs was further tested. After the cells were cultured in a proper induction medium for certain time, as shown in FIG. 4B, Alizarin Red S staining showed the formation of calcium nodules which verified that the hNCSCs-MSC were differentiated into osteocytes. Tuluidine Blue staining verified that the hNCSCs-MSC had been differentiated into chondrocytes, and formation of Oil Red O positive lipid droplets showed that the hNCSCs-MSC had been differentiated to adipocytes. As shown in FIG. 4C, after the cells were cultured in a proper differentiation medium for certain time, αSMA staining showed that the hNCSCs-MSC had been differentiated into smooth muscle cells. It indicates that the cultured hNCSCs have the multidirectional differentiation capacity.

Embodiment 2

Differentiation From Human Neural Crest Stem Cells (hNCSCs) to Leydig Cells (hiPS-hNCSCs-LCs or hNCSCs-LCs)

Figure 5:
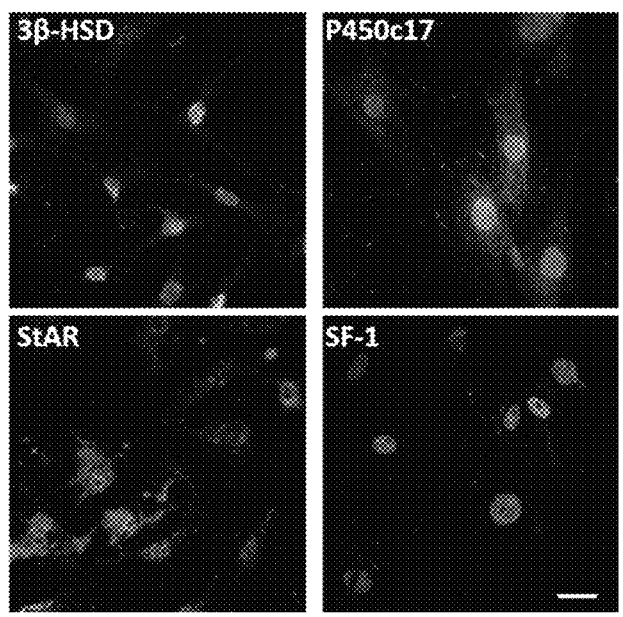
FIG. 5 shows a diagram of expression of Leydig cell (LC) markers in hNCSCs-LCs.
Figure 6:
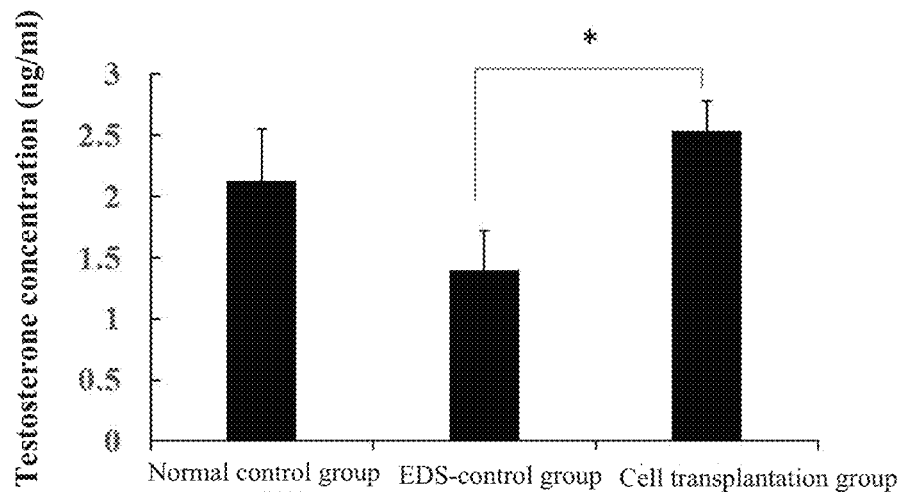
FIG. 6 is a diagram of testosterone secretion by hNCSCs-LCs under an in-vitro culture condition.

When the hNCSCs obtained by expansion reached the density of 60 percent confluence, the culture medium was replaced by a Leydig cells (LCs) differentiation culture medium (obtained by adding 2 volume percent of fetal calf serum (FCS), 1 nM of triiodothyronine (T3) (Sigma, T2877), 1 ng/ml of luteinizing hormone (LH) (Sigma, L6420), 70 ng/ml of an insulin-like growth factor (IGF-I) (PeproTech, 100-11), and 10 ng/ml of a platelet-derived growth factor BB (PDGF-BB) (PeproTech, 500-P47) into a DMEM-F12 culture medium (Hyclone, SH30023.018) for induction for 14 days and for cell differentiation, then cellular supernatant was collected, and cells were fixed by 4% PFA. Expression of mature LCs-related markers including 3β-HSD, P450c17, steroidogenic acute regulatory protein (StAR), and steroidogenic factor 1 (SF-1) were detected via immunofluorescence. As shown in FIG. 5, immunostaining analysis showed that cells (hNCSCs-LCs) differentiated from the hNCSCs expressed 3β-HSD, P450c17, StAR and SF-1. The testosterone level in the culture supernatant was tested via testosterone enzyme-linked immuno sorbent assay (ELISA) detection. As shown in FIG. 6, it revealed that the in vitro differentiated hNCSCs-LCs gradually secreted testosterone, which showed that the hNCSCs could be differentiated into mature LCs. (The LCs differentiation culture medium is not limited to the above-mentioned formula, and may still achieve the effects as shown in FIGS. 5 and 6 when adopting any one of specific combinations of the LCs differentiation culture medium obtained by adding 0.1 to 20 volume percent of FCS, 0.1 to 10 nM of T3, 0.1 to 20 ng/ml of LH, 5 to 100 ng/ml of the IGF-I, and 1 to 50 ng/ml of the PDGFBB into the DMEM-F12 culture medium.)

Embodiment 3

Effect of hiPS-hNCSCs-LCs (or hNCSCs-LCs) In Vivo

Figure 7:
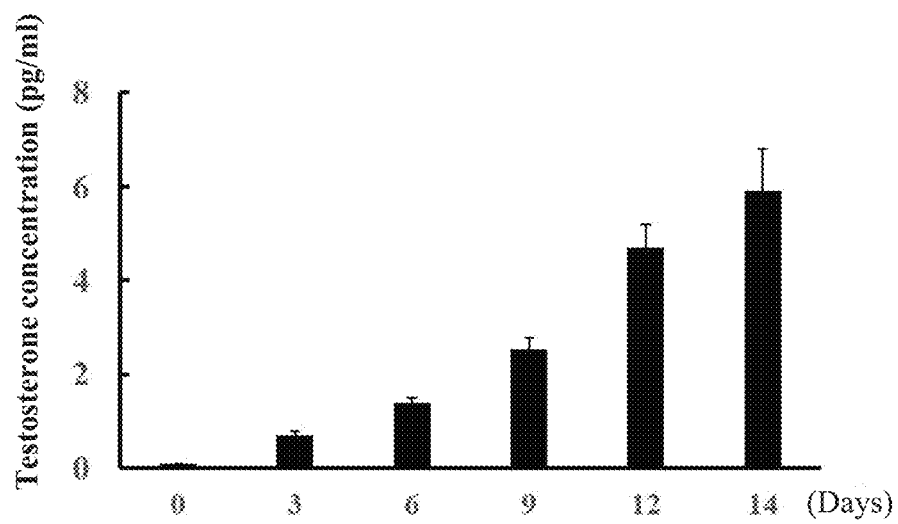
FIG. 7 is a diagram for describing the influence of hNCSCs-LCs transplantation on the serum testosterone level of an ethane dimethyl sulfonate (EDS) model rat.

The previous research showed that the Leydig cells in a rat could be exhausted 4 days after treated by a specific apoptosis inducer ethane dimethyl sulfonate (EDS), so that the EDS was injected to the abdominal cavity of the rat to establish an EDS model. Adult rats were randomly divided into three groups, including a normal control group, an EDS-control group and a cell transplantation group. For the rats in the normal control group, normal saline with the same volume was injected intraperitoneally respectively on the day 1 and the day 4. For the rats in the EDS-control group, EDS (75 mg/kg weight) was injected intraperitoneally on the first day, and 20 µl of normal saline (10 µl/unilateral testicle) was injected intraperitoneally on the day 4. For the rats in the cell group, EDS (75 mg/kg weight) was injected intraperitoneally on the day 1, and the hNCSCs-LCs (1.5×106 resuspended in 10 µl of PBS/unilateral testicle) cultured in an LC culture medium for 5 to 7 days were transplanted into the testicles of the rats on the day 4. On the day 10 of the transplantation, the serum testosterone concentration was tested. The result showed that the transplantation of hNCSCs-LCs can increase the serum testosterone level, as shown in FIG. 7.

It should be understood that the above-mentioned specific implementation modes of the present application are merely exemplarily description or explanation of the principle of the present application, but not deemed as limiting the present application. Therefore, any modifications, equivalent replacements and improvements that are made without departing from the spirit and scope of the present application shall all fall within the scope of protection of the present application. In addition, the attached claims of the present application aim at covering all changes and modifications, which fall within the scope and the boundary of the attached claims or within equivalent forms of this scope and boundary.

What is claimed is:

1. A method of committed differentiation of human induced pluripotent stem cells (hiPSCs) to Leydig cells (hiPS-hNCSCs-LCs), characterized in that, the method comprising:
   (1) performing differentiation on the human-induced pluripotent stem cells (hiPSCs) to obtain human neural crest stem cells (hiPS-hNCSCs) by culturing the hiPSCs in a neural differentiation culture medium to form embryoid bodies, and performing adherent culture of the embryoid bodies in a neural crest stem cell culture medium comprising basic fibroblast growth factor (bFGF) and epidermal growth factor (EGF); and
   (2) performing differentiation on the human neural crest stem cells (hiPS-hNCSCs) obtained in the step (1) to obtain the Leydig cells (hiPS-hNCSCs-LCs) by performing differentiation under adherent conditions on the hiPS-hNCSCs in a Leydig cells differentiation culture medium including triiodothyronine (T3), luteinizing hormone (LH), insulin-like growth factor 1 (IGF-1), and platelet-derived growth factor BB (PDGF-BB).

2. The method according to claim 1, wherein step (1) comprises inoculating the human-induced pluripotent stem cells (hiPSCs) into a culture dish with low attachment surface for culture.

3. The method according to claim 1 wherein at step (1), the hiPSCs are obtained by digesting and resuspending the hiPSCs prior to the performing differentiation, wherein the culturing of the hiPSCs to form EBs comprises culture on a bw attachment surface, and wherein the performing adherent culture of the EBs comprises culture on a fibronectin-coated culture dish, wherein the step (1) further comprises sorting through flow cytometry, the hiPS-hNCSCs obtained through adherent culture to obtain P75+/HNK1+double positive hiPS-hNCSCs and wherein the hiPS-hNCSCs used in step (2) are the P75+/HNK1+double positive hiPS-hNCSCs.

4. The method according to claim 3, wherein culture dish with low attachment surface is a Petri culture dish.

5. The method according to claim 1, wherein neural differentiation culture medium contains 50 to 80 volume percent of Knockout DMEM, 5 to 20 volume percent of Knockout SR, 0.5 to 5 volume percent of Penicillin-Streptomycin solution, 0.5 to 5 mM of L-glutamine, and 0.05 to 0.5 mM of β-mercaptoethanol.

6. The method according to claim 1, wherein neural differentiation culture medium contains 50 to 80 volume percent of Knockout DMEM, 5 to 20 volume percent of Knockout SR, 0.5 to 5 volume percent of Penicillin-Streptomycin solution, 0.5 to 5 mM of L-glutamine, and 0.05 to 0.5 mM of β-mercaptoethanol.

7. The method according to claim 1, wherein neural differentiation culture medium contains 80 volume percent of Knockout™ DMEM, 18 volume percent of Knockout™ SR, 1 volume percent of Penicillin-Streptomycin solution, 1 mM of L-glutamine, and 0.1 mM of β-mercaptoethanol.

8. The method according to claim 1, wherein neural crest stem cell culture medium contains 0.1 to 5 volume percent of N2, 0.5 to 10 volume percent of B27, 0.5 to 5 volume percent of Penicillin-Streptomycin solution, 0.5 to 5 mM of L-glutamine, and 0.05 to 0.5 mM of β-mercaptoethanol, and is further added with 1 to 100 ng/mL of a basic fibroblast growth factor (bFGF) and 1 to 100 ng/mL of an epidermal growth factor (EGF).

9. The method according to claim 1, wherein neural crest stem cell culture medium contains 1 volume percent of N2, 2 volume percent of B27, 1 volume percent of Penicillin-Streptomycin solution, 1 mM of L-glutamine, and 0.1 mM of β-mercaptoethanol, and is further added with 10 ng/mL of bFGF and 10 ng/mL of EGF.

10. The method according to claim 1, wherein neural crest stem cell culture medium is obtained by mixing a DMEM-F12 culture medium with a Neurobasal culture medium according to a ratio of 1:0.1-1, adding 0.1 to 5 volume percent of N2, 0.5 to 10 volume percent of B27, 0.5 to 5 volume percent of Penicillin-Streptomycin solution, 0.5 to 5 mM of L-glutamine, and 0.05 to 0.5 mM of β-mercaptoethanol, and further adding 1 to 100 ng/mL of bFGF and 1 to 100 ng/mL of EGF.

11. The method according to claim 3, wherein neural crest stem cell culture medium is obtained by mixing a DMEM-F12 culture medium with the Neurobasal culture medium according to a ratio of 1:1, adding 1 volume percent of N2, 2 volume percent of B27, 1 volume percent of Penicillin-Streptomycin solution, 1 mM of L-glutamine, and 0.1 mM of β-mercaptoethanol, and further adding 10 ng/mL of bFGF and 10 ng/mL of EGF.

12. The method according to claim 1, wherein step 1 further comprises expanding the hiPS-hNCSCs prior to the performing differentiation in to hiPS-hNCSCs-LCs.

13. The method according to claim 12, wherein at step (2) the Leydig cells differentiation culture medium is obtained by adding 0.1 to 20 volume percent of fetal calf serum (FCSD), 0.1 to 10 nM of triiodothyronine (T3), 0.1 to 20 ng/ml of leutenizing hormone (LH), 5 to 100 ng/ml of insulin-like growth factor (IGF-I) and 11 to 50 ng/ml of platelet-derived growth factor BB (PDGF-BB) to DMEM-F12 culture medium.

14. The method according to claim 12, wherein at step (2) the Leydig cells differentiation culture medium is obtained by adding 2 volume percent of fetal calf serum (FCS), 1 nM of triiodothyronine (T3), 1 ng/ml of luteinizing hormone (LH), 70 ng/ml IGF-I, and 10 ng/ml PDGF-BB to a DMEM-F12 culture medium.

* * * * *